United States Patent [19]
Pruitt, Sr.

[11] Patent Number: 5,993,382
[45] Date of Patent: Nov. 30, 1999

[54] LIGHTED CATHETER DEVICE AND METHOD FOR USE AND MANUFACTURE THEREOF

[75] Inventor: J. Crayton Pruitt, Sr., St. Petersburg, Fla.

[73] Assignee: Horizon Medical Products, Inc., Atlanta, Ga.

[21] Appl. No.: 08/757,856

[22] Filed: Nov. 27, 1996

[51] Int. Cl.$^6$ ........................................... A61B 1/07
[52] U.S. Cl. ........................................ 600/182; 604/101
[58] Field of Search ........................... 600/116, 162, 600/182; 604/280, 164, 283, 284, 96, 101, 102; 606/15

[56] References Cited

U.S. PATENT DOCUMENTS

| | | | |
|---|---|---|---|
| 3,516,408 | 6/1970 | Montanti | 604/284 |
| 4,734,094 | 3/1988 | Jacob | 604/284 |
| 5,273,534 | 12/1993 | Knoepfler | 604/284 |
| 5,330,467 | 7/1994 | Abela | 606/15 |
| 5,380,317 | 1/1995 | Everett | 606/15 |
| 5,522,868 | 6/1996 | Buckley | 607/94 |
| 5,586,982 | 12/1996 | Abela | 606/15 |
| 5,613,949 | 3/1997 | Miraki | 604/284 |
| 5,649,924 | 7/1997 | Everett | 606/15 |
| 5,695,482 | 12/1997 | Kaldany | 604/280 |
| 5,762,604 | 6/1998 | Kieturakis | 604/164 |
| 5,782,825 | 7/1998 | Anderson | 606/15 |

*Primary Examiner*—John P. Leubecker
*Attorney, Agent, or Firm*—Needle & Rosenberg, P.C.

[57] ABSTRACT

A lighted catheter device employing an optical fiber having a core and a cladding, the cladding providing internal reflection, the fiber being substantially without the cladding at an end portion to permit light to escape laterally thereat, for illumination in a catheter device. A lighted carotid shunt, a lighted occluder incorporating the fiber and lateral illumination method are described.

11 Claims, 3 Drawing Sheets

LIGHTED CATHETER DEVICE AND METHOD FOR USE AND MANUFACTURE THEREOF

BACKGROUND OF THE INVENTION

This invention relates to a catheter device for use in a blood vessel, particularly such a device employing a light source by which to illuminate the blood vessel.

There are presently a multitude of means by which catheter devices have been provided a light source for illumination of a blood vessel. Such means typically employ one or more optical fibers, for transmitting light of a selected frequency, the optical fibers terminating within the catheter at a predetermined position, the area around which it is desired to illuminate.

Because optical fibers are designed to guide light from one end of the fiber to the other, by causing the light to internally reflect, the light typically exits the fibers in substantially the direction along which the fiber is aligned. In a catheter device, this direction is typically also aligned with the blood vessel, owing to the need to maintain compact lateral dimensions. Thence, light leaving the fiber is generally not available for lateral illumination of the vessel walls unless the end of the fiber is treated in some manner to alter the course of light traveling therethrough from a generally forward direction to a lateral direction.

There are a number of references that treat or adapt the tip of an optical fiber in various ways to project light laterally onto a surface to be viewed. Examples are Ishibashi et al., U.S. Pat. No. 4,272,156 ("Ishibashi"), employing angled exit end faces of a fiber; Heller, U.S. Pat. No. 4,567,882 ("Heller"), employing a prism or bifurcated emitter portion of a fiber; Ector, U.S. Pat. No. 4,658,816 ("Ector"), employing a hemispherical tip formed on the end of a fiber; Mackin, U.S. Pat. No. 4,961,738 ("Mackin"), employing diverging optical fibers; Sugiyama et al., U.S. Pat. No. 5,036,834 ("Sugiyama"), employing a lens in close proximity to the end of a fiber; and Kozawa et al., U.S. Pat. No. 5,335,648 ("Kozawa"), employing a mirror member arranged at the outgoing end of a fiber.

All of the aforementioned approaches have drawbacks, however. Ishibashi requires a multitude of fibers having faces angled in different directions to project light laterally over a wide area. Requiring a large number of specially treated fibers is costly and demanding of valuable space, especially in a catheter device. Heller and Sugiyama require the cost and assembly complexity associated with an additional, precision part. Ector requires the manufacturing complexity and cost of forming a hemispherical end on a fiber. Mackin requires the manufacturing complexity and cost of creating a diverging optical fiber, as well as demands the space within the catheter to permit the divergence. Kozawa, as well, requires the cost of an additional part, complex assembly, and valuable space. All of the foregoing approaches require a relatively precise manufacturing process to achieve their aims.

Therefore, there is a need for a novel lighted catheter device and method for use and manufacture thereof that does not require precise manufacturing or complex assembly, and which requires minimal space.

SUMMARY OF THE INVENTION

The lighted catheter device and method of use and manufacture thereof of the present invention solves the aforementioned problems and meets the aforementioned needs by providing, in a catheter device, an optical fiber having a core and a cladding, the core having a higher index of refraction than the cladding so as to cause internal reflection of light transmitted through the core, an end portion of the optical fiber being substantially without the cladding to permit light to escape laterally therefrom.

In a first embodiment of the invention, the optical fiber is employed in a carotid shunt device having three lumens in a tube. The tube has tips at first and second ends. A first smaller balloon is bonded to the exterior of the tube proximate the first tipped end. A second larger balloon is bonded to the exterior of the tube proximate the second tipped end. Each balloon is in fluid communication with a respective one of the lumens. Another lumen is employed for carrying the optical fiber. The optical fiber is disposed proximate the first balloon, between the first balloon and the second balloon. The remaining lumen is employed for shunting.

In a second embodiment of the invention, the optical fiber is employed in an occluder device (e.g., occlusion catheter) or other catheter device having a single lumen in a tube. The tube is tipped at one end and open at the other end. A balloon is bonded to the exterior of the tube proximate the tipped end, the balloon being in communication with the lumen. The optical fiber is carried within the lumen. The fiber is disposed proximate the balloon, between the balloon and the tipped end. The invention may also be employed in multiple lumen catheters and other catheters where lumen size, vessel size and technical parameters require or permit such a configuration. For example, an irrigation lumen may be employed in a device employing the present invention. Also, an additional lumen may be employed to contain the fiber in such a device where a single lumen therefor might become blocked.

Therefore, it is a principal object of the present invention to provide a novel lighted catheter device.

It is another object of the present invention to provide such a device that reduces manufacturing complexity and required precision.

It is still another object of the present invention to provide such a device that reduces assembly complexity.

It is a further object of the present invention to provide such a device that reduces cost.

The foregoing and other objects, features and advantages of the present invention will be more readily understood upon consideration of the following detailed description of the invention, taken in conjunction with the following drawings.

DETAILED DESCRIPTION OF A PREFERRED EMBODIMENT

Figure 1B:
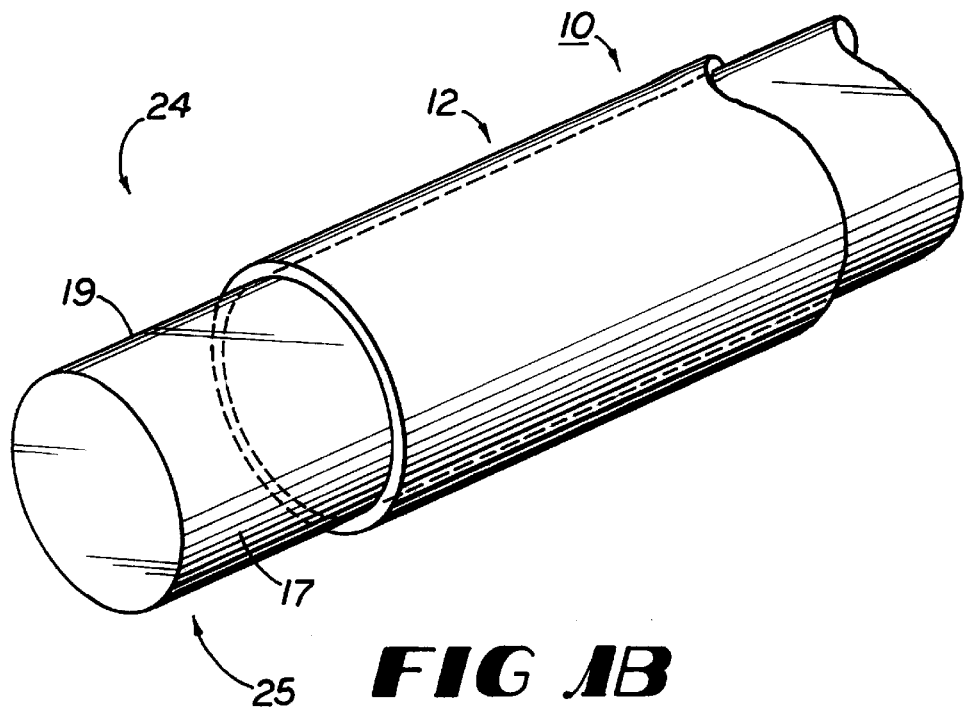
FIG. 1B is a pictorial view of the fiber of FIG. 1A adapted according to the present invention.
Figure 1A:
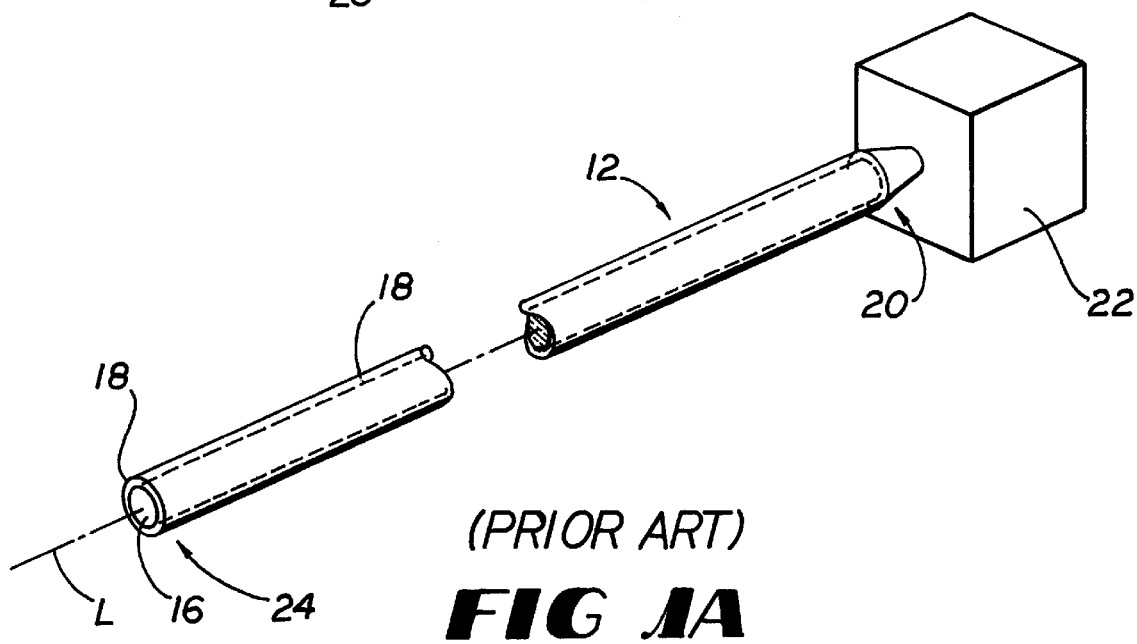
FIG. 1A is a pictorial view of a prior art optical fiber.

Referring to FIGS. 1A and 1B, an illumination member 10 for a lighted catheter will first be described. The illumination member 10 is disposed within a lumen of the catheter as will be described below. The catheter is generally employed inside a blood vessel of a patient, but may be employed in other internal body structures as well.

The illumination member 10, preferably comprising an elongate optical fiber 12, which may be an optical fiber bundle, defines a longitudinal axis L, aligned substantially with the fiber 12. All directions off the axis L are referred to herein as lateral directions.

Referring to FIG. 1A, the fiber 12 comprises a core portion 16 having a first index of refraction n1 and a cladding portion 18 having a second index of refraction n2. The index of refraction n1 is provided to be greater than the index of refraction n2, to cause internal reflection of a substantial amount of light which is injected into the core portion. Such a fiber 12 is manufactured and marketed by Poly-Optical Products, Inc., of Irvine, Calif., as an optical grade acrylic optical fiber under the trademark "LUMI-LEEN." The fiber so provided has a core refractive index of 1.492 and a cladding refractive index of 1.417. However, other combinations of core and cladding refractive indices achieving internal reflection in the optical fiber 12 may be employed without departing from the principles of the invention. Moreover, the fiber 12 may also comprise a protective layer, which is sometimes also referred to as a cladding in the optical fiber art, without departing from the principles of the invention. The aforedescribed optical fiber has a core portion comprising polymethyl methacrylate and a cladding portion comprising a fluorinated polymer, wherein 95% to 98% of the fiber diameter is occupied by the core portion.

Light is injected into the fiber 12 at an input end 20 with a light source 22 in any convenient manner known in the art. In a hospital, the light source 22 will generally be available for other procedures and will employ a fiber connection to which the end 20 of the fiber 12 will be advantageously adapted. The light source 22 preferably provides visible light only, with infra-red and ultra-violet filtered either at the source or the connection of the fiber thereto, or by means of the fiber itself, to protect the internal tissues of the patient.

Optical fibers, such as the fiber 12 depicted in FIG. 1A, are normally adapted to transmit light substantially along the longitudinal axis, and to emit the light along that axis at an end thereof. In the illumination member 10, however, the fiber 12 is adapted to disperse in a lateral direction light which is transmitted therethrough, preferably at an end portion 24 thereof (FIG. 1B). Moreover, it is preferable that the fiber 12 is adapted to disperse light substantially equally in all lateral directions, so that a substantially cylindrical source of light is provided at the end portion 24 of the illumination member 10.

To provide for light dispersal, the fiber 12 is provided without some or all of the cladding 18 along the side 19 thereof at a selected illumination output portion 25, so that the core 16 is exposed thereat. As aforementioned, the cladding 18 in combination with the core 16 of the fiber provides for lateral internal reflection of light transmitted therethrough. Thence, at the illumination output portion 25, where the core 16 is exposed, light traveling through the core may escape laterally rather than be confined by the cladding 18 to travel forwardly.

The fiber 12 so provided has its core 16 generally extending a predetermined distance beyond its cladding 18 to form a substantially cylindrical exposed core 17, although other selected areas of the core 16 could be exposed without departing from the principles of the invention. For example, apertures could be provided in the cladding 18 wherever desired.

Having described an illumination member according to the present invention, two preferred embodiments of the invention employing the illumination member will next be presented.

Figure 2A:
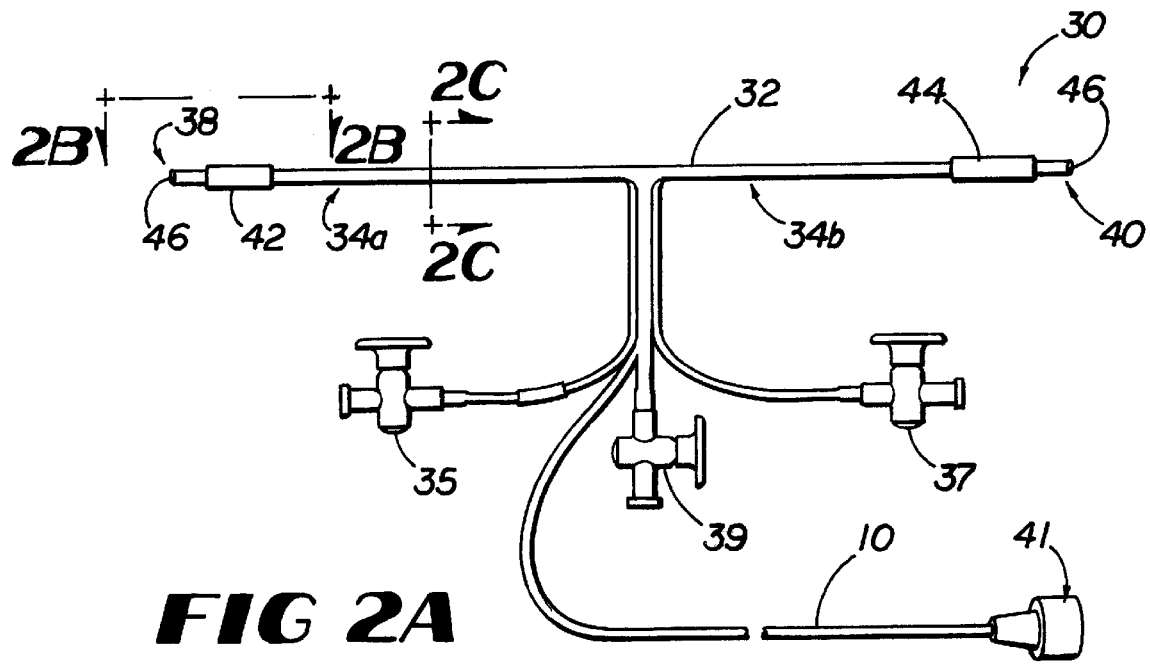
FIG. 2A is a side elevation of a carotid shunt device employing the optical fiber of FIG. 1B, according to the present invention.
Figure 2B:
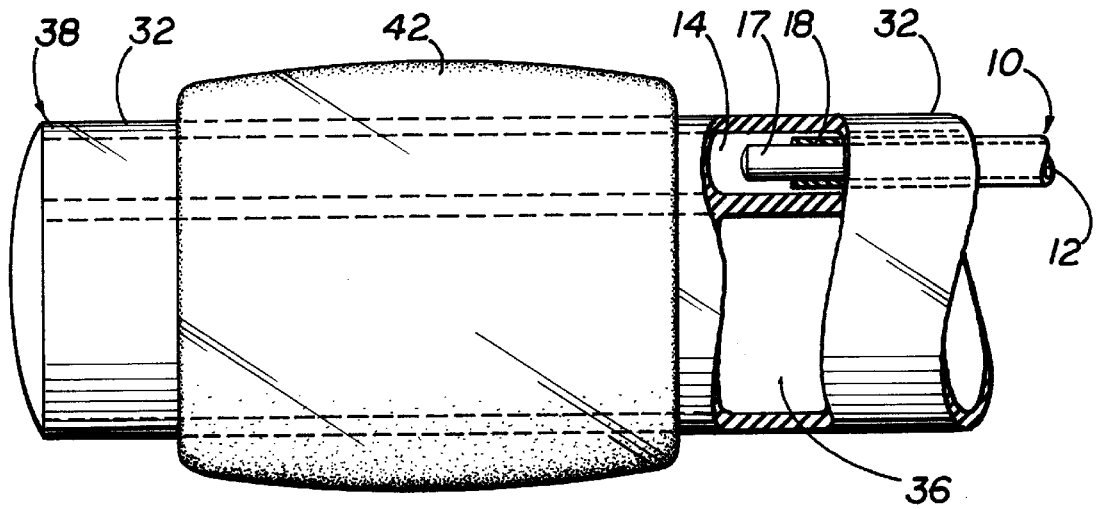
FIG. 2B is a side elevation of an end of the carotid shunt device of FIG. 2A, with a portion cut away to show the interior thereof.
Figure 2C:
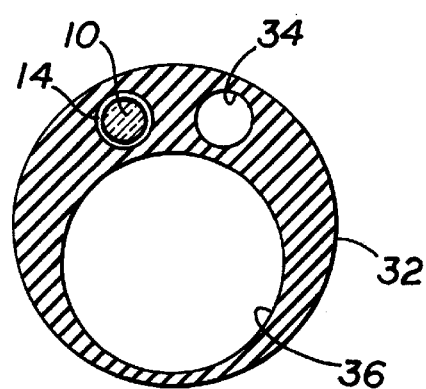
FIG. 2C is a cross-section of a tube of the carotid shunt device of FIG. 2A, according to the present invention.

Referring to FIGS. 2A–2C, in a first preferred embodiment of the invention, the illumination member 10 is employed in a carotid shunt device 30 for use in a blood vessel. The shunt device 30 has a tube 32 within which are included a first lumen 34, a second lumen 14 and a third lumen 36. The first lumen is divided into two parts 34a and 34b, corresponding to respective ends of the shunt, the parts 34a and 34b being sealed from one another. The tube 32 is tipped at a first end 38 and a second end 40 thereof, to stop fluid communication from the first lumen 34 and the second lumen 14 beyond the first end 38 and the second end 40 of the tube, respectively, the third lumen 36 remaining open to fluid communication with the blood vessel at apertures 46. The third lumen 36 is, preferably, also in fluid communication with an access valve 39.

A first, preferably smaller, balloon 42 is bonded to the exterior of the tube 32 in any convenient manner known in the balloon catheter art. The balloon 42 is disposed proximate the first end 38. A second, preferably larger, balloon 44 is likewise bonded to the exterior of the tube, proximate the second end 40. Each balloon is in fluid communication with the respective parts 34a and 34b of the first lumen 34. Each respective portion of the first lumen 34 is in turn, in fluid communication with a respective fluid inlet valve 35 and 37, for connection to an inflation source (not shown).

The second lumen 14 is employed for carrying the illumination member 10, which is disposed therein so that the end portion 24 is disposed proximate the first balloon 42, between the first balloon and the second balloon 44. An optical connection 41 for receiving a light source is deposed at the other end of the illumination member 10. The third lumen 36 is employed for shunting, through the apertures 46, as is known in the art.

The tube 32 may be made of a single part, but may advantageously be made of two parts corresponding to the lumens 34a and 34b. The parts may be of different sizes, and may employ different numbers of lumens. For example, the end 38 of the tube could be a different size than the end 40.

Figure 3A:
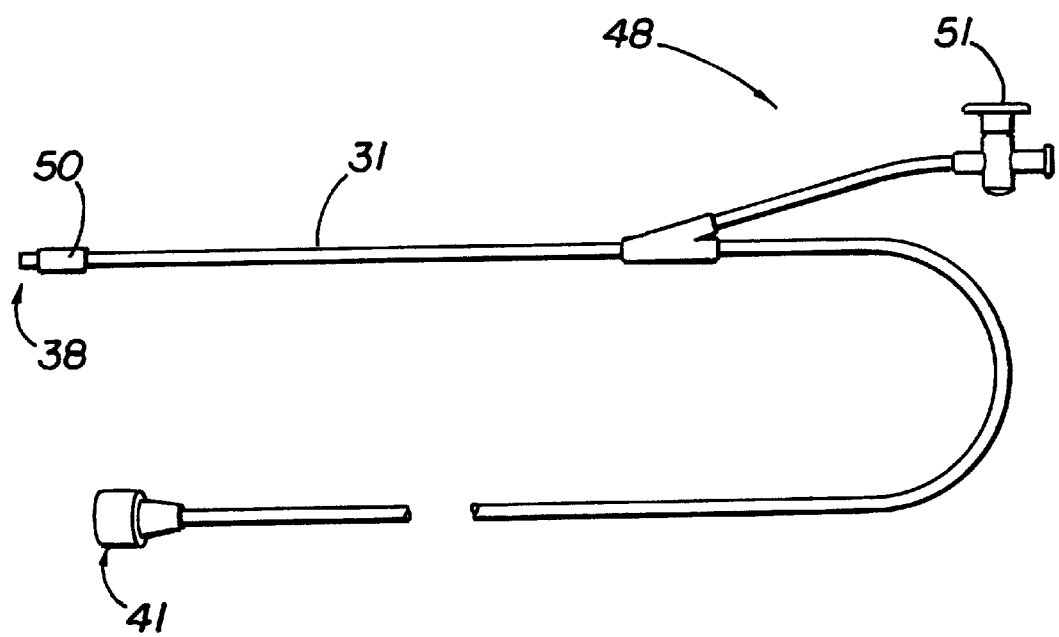
FIG. 3A is a side elevation of an occluder device employing the optical fiber of FIG. 1B, according to the present invention.
Figure 3B:
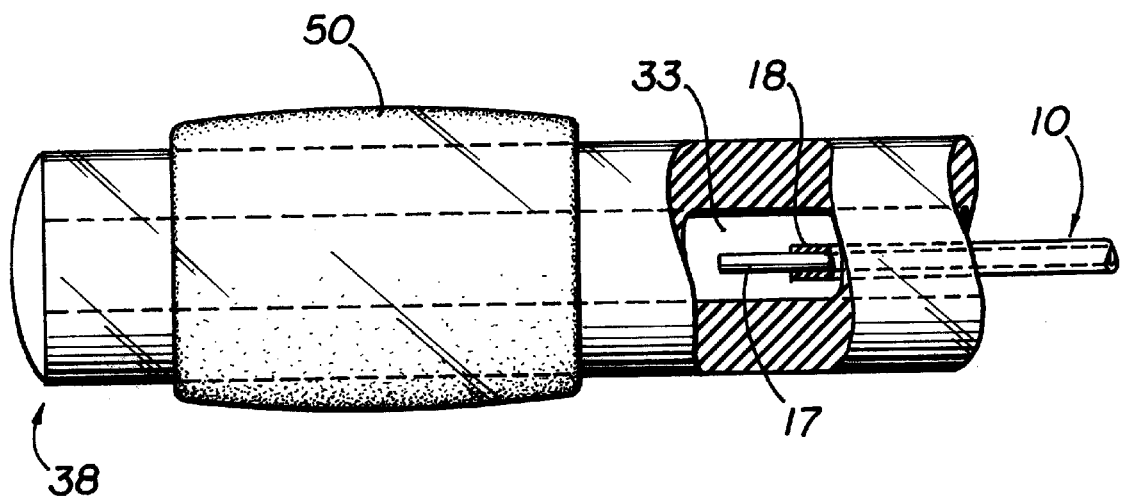
FIG. 3B is a side elevation of an end of the occluder of FIG. 3A, with a portion cut away to show the interior thereof.

Referring to FIGS. 3A–3B, in a second preferred embodiment of the invention, the illumination member 10 is employed in an occluder device 48 for use in the blood vessel. The occluder device 48 comprises a catheter 31, having first lumen (not shown) and a second lumen 33. The catheter 31 is tipped at a first end 38, to stop fluid from entering the first lumen or the second lumen 33.

A balloon 50 is bonded to the exterior of the catheter 31 in any convenient manner known in the balloon catheter art. The balloon 50 is disposed proximate the first end 38. The balloon 50 is in fluid communication with the first lumen which, in turn, is in fluid communication with an inlet valve 51 for connection to an inflation source (not shown).

The second lumen 33 is employed for carrying the illumination member 10, which is disposed therein so that the end portion 24 is disposed proximate the balloon 50. An optical connection 41 for receiving a light source is deposed at the other end of the illumination member 10.

METHOD FOR MANUFACTURE

The fiber may be provided as aforedescribed either in the initial manufacture thereof or the fiber may be adapted, preferably with the use of automated machinery, by removing existing cladding ("decladding") at the output 25. Decladding e.g., can be by abrading or scraping. Decladding by hand has been found to be easily done by light scraping.

METHOD FOR USE

The lighted catheter device of the present invention is employed in, e.g, a shunt or an occlusion catheter to illuminate the interior of a vessel, such as a blood vessel, so the surgeon can directly visualize the end point of the plaque that has formed therein. The surgeon can therefore be sure that all of the plaque is removed without having to increase the length of the arteriotomy even for high plaque lesions. When a cleaned artery is sewn up, its diameter becomes slightly smaller in the region of the arteriotomy, due to the suturing. Blood flow is consequently impeded in the region, as a result of the decreased diameter of the vessel. The present invention advantageously permits a shorter arteriotomy, to result in a smaller region of reduced diameter after closing.

It is to be recognized that, while a specific lighted catheter device and method of use and manufacture thereof has been shown as preferred, other configurations could be employed, in addition to configurations already mentioned, without departing from the principles of the invention. For example, other means of adapting the fiber 12 to prevent internal reflection at the end portion 24, and other means of providing a fiber without cladding at the end portion may be employed, and the fiber 12 may be employed in other catheter devices than those aforedescribed.

The terms and expressions which have been employed in the foregoing specification are used therein as terms of description and not of limitation, and there is no intention of the use of such terms and expressions of excluding equivalents of the features shown and described or portions thereof, it being recognized that the scope of the invention is defined and limited only by the claims which follow.

I claim:

1. A carotid shunt device, comprising:
    a tube having a first end, a second end, a first lumen, a second lumen and a third lumen, wherein said first and second lumens are tipped at said first and second ends to stop fluid communication of said first and second lumens beyond said first and second ends;
    a first balloon disposed proximate said first end, said balloon being bonded to the exterior of said tube and being in fluid communication with said first lumen;
    a second balloon disposed proximate said second end, said second balloon being bonded to the exterior of said tube and being in fluid communication with said first lumen, wherein said first lumen is in fluid communication with an inflation source; and
    an illumination member comprising an elongate light transmitting core adapted to transmit light from a light source input to an illumination output, said illumination output being disposed on a side thereof, a cladding substantially surrounding said core and being adapted to confine said light substantially therewithin, said core being coupled to the light source to permit injection of illuminating light into said core, said core being at least partly exposed at said illumination output, to permit said illuminating light to escape laterally from said core, wherein said illumination output is at an end of said light transmission member, wherein said light transmitting core extends a predetermined distance beyond said cladding at said illumination output, and wherein said illumination output is disposed proximate said first balloon, between said first balloon and said second balloon.

2. The shunt device of claim 1, wherein said first lumen is divided into a first part communicating with said first balloon, and a second part communicating with said second balloon.

3. The shunt device of claim 2, wherein said first part of said first lumen is in fluid communication with a first fluid inlet valve for connection to an external inflation source, and said second part of said first lumen is in fluid communication with a second fluid inlet valve for connection to an external inflation source.

4. The shunt device of claim 1, wherein said first balloon is smaller than said second balloon.

5. An occluder device, comprising:
    a tube having a first end, a second end and a first lumen, wherein said first lumen is tipped at said first end to stop fluid communication of said first lumen beyond said first end;
    a balloon disposed proximate said first end, said balloon being bonded to the exterior of said tube and being in fluid communication with said a first lumen, wherein said a first lumen is in fluid communication with an inflation source; and
    an illumination member comprising an elongate light transmitting core adapted to transmit light from a light source input to an illumination output, said illumination output being disposed on a side thereof, a cladding substantially surrounding said core and being adapted to confine said light substantially therewithin, said core being coupled to the light source to permit injection of illuminating light into said core, said core being at least partly exposed at said illumination output, to permit said illuminating light to escape laterally from said core, wherein said illumination output is at an end of said light transmission member, wherein said light transmitting core extends a predetermined distance beyond said cladding at said illumination output, and wherein said illumination output is disposed proximate said balloon, between said balloon and said second end.

6. The occluder device of claim 5, further comprising a second lumen for carrying the illumination member.

7. The occluder device of claim 5, wherein said first lumen is in fluid communication with a fluid inlet valve for connection to an external inflation source.

8. A method of providing lateral illumination in a carotid shunt device, comprising the steps of:
    providing an illumination member comprising an elongate light transmitting core adapted to transmit light from a light source input to an illumination output, said illumination output being disposed on a side thereof, a cladding substantially surrounding said core and being adapted to confine said light substantially therewithin, said core being coupled to the light source to permit injection of illuminating light into said core, said core being at least partly exposed at said illumination output, to permit said illuminating light to escape laterally from said core;
    inserting said illumination output into a lumen of a carotid shunt device;
    inserting said carotid shunt device in a carotid artery of a patient; and
    positioning said illumination output in said lumen at a selected location in said device so that said illumination output is disposed to illuminate laterally a selected portion of said carotid artery.

9. The method of claim 8, wherein said positioning is by feeding said illumination member through said lumen.

10. A method of providing lateral illumination in an occluder device, comprising the steps of:

providing an illumination member comprising an elongate light transmitting core adapted to transmit light from a light source input to an illumination output, said illumination output being disposed on a side thereof, a cladding substantially surrounding said core and being adapted to confine said light substantially therewithin, said core being exposed at said light source input to permit injection of illuminating light into said core, said core being at least partly exposed at said illumination output, to permit said illuminating light to escape laterally from said core;

inserting said illumination output into a lumen of an occluder device;

inserting said occluder device in a vessel of a patient; and positioning said illumination output in said lumen at a selected location in said device so that said illumination output is disposed to illuminate laterally a selected portion of said vessel.

11. The method of claim 10, wherein said positioning is by feeding said illumination member through said lumen.

* * * * *